United States Patent
Niiranen et al.

(10) Patent No.: US 9,097,666 B2
(45) Date of Patent: Aug. 4, 2015

(54) METHOD AND DEVICE FOR MEASURING GAS COMPONENT CONCENTRATION INSIDE A GLASS UNIT

(75) Inventors: Kai Niiranen, Jarvenpaa (FI); Erno Launo, Helsinki (FI)

(73) Assignee: OY SPARKLIKE AB, Helsinki (FI)

(*) Notice: Subject to any disclaimer, the term of this patent is extended or adjusted under 35 U.S.C. 154(b) by 73 days.

(21) Appl. No.: 14/118,251

(22) PCT Filed: May 18, 2012

(86) PCT No.: PCT/FI2012/050474
§ 371 (c)(1),
(2), (4) Date: Dec. 11, 2013

(87) PCT Pub. No.: WO2012/156589
PCT Pub. Date: Nov. 22, 2012

(65) Prior Publication Data
US 2014/0092379 A1   Apr. 3, 2014

(30) Foreign Application Priority Data
May 18, 2011   (FI) .................................. 20115482

(51) Int. Cl.
*G01N 21/00* (2006.01)
*G01N 21/61* (2006.01)
(Continued)

(52) U.S. Cl.
CPC .............. *G01N 21/61* (2013.01); *G01B 11/06* (2013.01); *G01J 3/443* (2013.01); *G01N 21/39* (2013.01); *G01N 21/55* (2013.01); *G01N 21/031* (2013.01); *G01N 21/67* (2013.01); *G01N 2021/0396* (2013.01)

(58) Field of Classification Search
USPC ............................................... 356/301, 72–73
See application file for complete search history.

(56) References Cited

U.S. PATENT DOCUMENTS

| 5,650,845 A | 7/1997 | Kebabian |
| 6,091,504 A | 7/2000 | Walker et al. |

(Continued)

FOREIGN PATENT DOCUMENTS

WO    2011007047    1/2011

OTHER PUBLICATIONS

Kebabian et al., "Determination of argon-filled insulated glass window seal failure by spectroscopic detection of oxygen", Institute of Physics Publishing, Measurement Science and Technology, 2003, vol. 14, pp. 983-988, XP001169658.
(Continued)

*Primary Examiner* — Abdullahi Nur
(74) *Attorney, Agent, or Firm* — Young & Thompson

(57) ABSTRACT

A non-invasive method for determining a concentration of a gas component in a gas mixture contained in a spacing of a glass unit having at least two glass sheets spaced apart from each other and forming the spacing. One or more light beams is applied at an angle to the surface of the glass unit, wherein the wavelength of the emitted light beam is varied around or over the at least one absorption line of the interest gas component. The light beams transmitted through or reflected from at least one surface or interface locating at the opposite side of the spacing are collected by a detector and non-linear variations in the intensity of the transmitted or reflected light beams over an absorption line of the interest gas is then component determined. The concentration of the gas component to be measured is determined based on the non-linear variations in the intensity.

21 Claims, 3 Drawing Sheets

(51) Int. Cl.
  *G01N 21/39* (2006.01)
  *G01B 11/06* (2006.01)
  *G01J 3/443* (2006.01)
  *G01N 21/55* (2014.01)
  *G01N 21/03* (2006.01)
  *G01N 21/67* (2006.01)

(56) References Cited

U.S. PATENT DOCUMENTS 6,304,362 B1 * 10/2001 Zheludev et al. ............ 359/241
6,639,678 B1   10/2003 Veale 2005/0286054 A1  12/2005  Chen et al.
2006/0044562 A1   3/2006  Hagene et al.
2007/0103686 A1   5/2007  Tornkvist et al.
2010/0067012 A1   3/2010  Tondello et al.

OTHER PUBLICATIONS

International Search Report dated Sep. 25, 2012, corresponding to PCT/FI2012/050474.

Werle, et al.; Near-and Mid-Infrared Laser-Optical Sensors for Gas Analysis. Optics and Lasers in Engineering. 2002, vol. 37, pp. 101-114.

* cited by examiner

METHOD AND DEVICE FOR MEASURING GAS COMPONENT CONCENTRATION INSIDE A GLASS UNIT

TECHNICAL FIELD OF THE INVENTION

The invention relates to a method and device for measuring a gas component concentration inside a glass unit of one or several separate cavities or any other similar transparent container. In addition the invention relates to measuring the glass unit of one or several separate cavities or any other similar transparent container dimensions, laminations and metallic coatings.

BACKGROUND OF THE INVENTION

In the glass manufacturing process glass sheets (known as float glass) can be combined with different kind of elements, such as coated or tempered layers to create glass panes for different purposes having specific properties. For example, insulating glass units, IGUs, are constructed typically with a configuration having two or more glass sheets with a closed spacing in between the sheets, where the closed spacing is filled with gas with low thermal conductivity, such as Oxygen, Argon, Xenon, Krypton Nitrogen or mixture of those.

In addition to gases with low thermal conductivity, also low emissivity coatings are used for a considerable reduction of heat transfer in window glazing units. Most of the commercial coatings have metallic substances in them and are thus electrically conductive. They reflect also visible light better than the bare glass surface. Since the low emissivity coating is typically inside an insulating glass unit for mechanical and chemical protection, it cannot be directly accessed for conductivity measurement.

When glass panes are manufactured, their quality must be evaluated according to the manufacturer's quality system, standards or local regulations. The most typical parameters of a glass pane are its mechanical dimensions, thickness of the glass panes, thickness of the possible lamination(s) or coating(s), spacing between the panes, locations of the possible surface coatings and possible toughening or tempering of the glass panes, but also the concentration of the gas component(s) in the spacing.

Different kinds of solutions are known from the prior art for determining the concentration of gas components in a gas mixture contained in the spacing, such as taking a gas sample from the spacing and measuring it e.g. by using a mass spectrometer. Taking the gas sample is invasive method, whereupon the surface of the glass unit must be broken, which is clear disadvantage of the invasive methods. Also non-invasive methods are known, such as discharging the spacing between the panels of the glass unit by applying rapidly alternating electrical field to the spacing, and analyzing the emitted discharge light. The discharge can be created by a needle-like electrode, whereupon the inner coating layer of the glass unit made of conducting material is used as another electrode.

There are also some drawbacks with the known non-invasive methods. For example if the glass pane is coated or laminated with plastic film, another electrode must be provided in another way. In addition when at least one sheet has a metallically coated surface, the measurement cannot be done through the metallic surface, since the rapidly alternating electrical field cannot penetrate the metallic surface. Furthermore only one spacing can be measured at a time.

SUMMARY OF THE INVENTION

An object of the invention is to alleviate and eliminate the problems relating to the known prior art. Especially the object of the invention is to provide a method for performing a non-invasive determining a concentration of a gas component in a gas mixture contained in a spacing of a glass unit independently of possible coating material. An additional object of the invention is to provide a method for determining a concentration of gas components in each spacing separately at a same time.

The object of the invention can be achieved by the features of independent claims.

The invention relates to a device according to claim 1. In addition the invention relates to a device or arrangement of claim 14.

According to an embodiment a concentration of a gas component in a gas mixture contained in a spacing of a glass unit having at least two glass sheets spaced apart from each other and forming said spacing is determined non-invasively. In the method at least one light beam is applied at an angle to the surface of said glass unit and the wavelength of the emitted light beam is varied around or over the at least one absorption line of the interest gas component. The light beams reflected from at least one surface or interface locating at the opposite side of the gas filled spacing is collected on a detector. According to another embodiment the measurement can be a through measurement, whereupon the light emitting means and the detector locate at the opposite side of the glass unit and the light beams transmitted through the glass unit are determined by the detector. The gas component in said spacing absorbs a very narrow-linewidth characteristic for each gas component, and the magnitude of the intensity variation due to absorption is proportional to the concentration of the gas. The intensity variations around or over the absorption line of the interest gas component is very non-linear. In the invention these non-linear variations in the intensity of the reflected or transmitted light beams around or over an absorption line of the interest gas component is then determined for determining the concentration of the gas component.

According to an exemplary embodiment the concentration of the gas component can be determined e.g. by comparing the magnitude of the intensity variations to reference intensity variations, such as the intensity variations of different concentrations of said gas measured or in other way known beforehand.

According to an embodiment a reflector is used at the opposite side of the glass unit as a surface or interface reflecting the emitted light beam back through the glass unit on the detector. When using the reflector the intensity of the reflection is typically more intensively than the reflection from any other surfaces. It is to be noted that the determined concentration measured in this way from the intensity variation(s) at the absorption line(s) when varying the wavelength of the emitted light beam over the absorption line(s) is the average concentration over the (all) measured space(s). However, the higher intensity of the reflection enables more accurate analysis. In addition it is to be noted that the reflection measurement allows long measuring distance (since the light beam travels twice the distance compared to transmission measurement), whereupon the measuring accurate is very good also for small concentrations. Furthermore the reflection measurement enables the measuring from one side which is clear benefit in some cases.

It is to be noted that according to an embodiment of the invention the surface or interface reflecting the beam may also be a surface or interface of the glass sheet faced towards said spacing comprising the gas component either as alone or in addition the additional reflector, and that the reflections from each surfaces or interfaces can be measured and intensity variations in these reflections determined in order to determine the gas concentration possibly even in each spacing. The spacing comprising the gas component concentration and thereby causing said non-linear intensity variation can be determined by orders of the beams on the detector reflected from the surfaces or interfaces of the glass sheets of the glass unit.

Another way is to use essentially a constant beam angle, but change the distance of the measuring unit (said unit comprising the light emitting means as well as the detector) from the surfaces (outer but also from inner surfaces) of the glass unit and thereby determine the maxims of the intensities. Still according to another embodiment the mutual angle of the light emitting means and the detector may be changed and thereby determine the surfaces from the intensity maxims. Each of the intensity maximum corresponds one surface of the glass unit.

According to an embodiment also interface type and/or possible coatings (such as laminations or metallic coatings) of the glass sheet in question can be determined. This is possible according to the invention when the intensities of the reflected beams from different type of surfaces with a certain light source are known beforehand. For instance the intensity of the beam reflected by the low emissivity surface (metal coating and thus conductive surface) is much greater (typically 5 or even 10 times) than the intensity of the beam reflected by the surface without any coating (non-conductive surfaces). In addition there are essentially no intensity variations in the reflections from the coatings over the used wavelengths.

According to an embodiment the intensity of the reflected beam is determined and compared to the intensities stored advantageously for example into a memory means and if the detected intensity is clearly greater than the intensity of the beam reflected from the non-conducting surfaced, it can be indicated automatically that the determined object comprises the low emissivity surface. Even the material of the coating can be determined based on the intensities characteristic for different coatings. This can be done e.g. by selecting the interface type and/or coating type the known intensity of which best matches with the measured intensity. Also the location of the coating can be determined by orders of the beams on the detector reflected from said coating.

In addition also the thickness of a layer between two interfaces or surfaces of the glass unit can be determined based on the locations of the light beams reflected from the first and second interfaces on the detector, as well as also the distance between two sheets, such as outermost and innermost sheets, based on the locations of the light beams reflected from the corresponding sheets on the detector and the refractive index of said material of the sheets. This is also possible with the measuring unit comprising the light emitting means as well as the detector, where the distance of said unit is varied from the surface(s) of the glass unit or the angle of said light emitting means and the detector, as is illustrated in connection with e.g. FIGS. 2C, 2D.

The light beams applied are advantageously laser light beams provided by a tunable-diode-laser-absorption-spectroscopy (TDLAS) technique. The used laser frequency can be by tuned around or over an absorption line of the interest gas component, whereafter the variations in reflected intensity is measured.

The measurements are governed by the Beer-Lambert-Bouguer law, which describes how the light intensity decreases upon interaction with absorbing materials as follows:

$$I = I_0 e^{-\sigma(\nu)NL}$$

where $\nu$ is the frequency [Hz], $I_0$ and $I$ [W] are the initial and transmitted intensities respectively, $\sigma(\nu)$ [cm2/molecule] the frequency-dependent absorption cross section of the gas of interest, N [molecule/cm3] the number concentration of molecules of that gas, and L [cm] the pathlength. FIG. 1(a) shows the detected intensity I($\nu$) of the reflected beam, where the weak absorption is barely seen. FIG. 1(b) shows the intensity of said reflected beam calculated using a second-order baseline estimation of $I_0(\nu)$ (i.e. a $2^{nd}$ order polynomial fitted to the edges of the detected signal).

The absorption signal to be detected is manipulated by WMS or FMS technique, such as by scanning a sinusoidally frequency-modulated diode laser over the absorption feature of the gas component to be determined in order to strengthen the second order polynomial fitted to the non-linear curve representing the variation in the intensity of the detected beams and concentration of the gas component to be detected and/or to minimize the low-frequency noise induced.

The performance of direct absorption is often degraded by the occurrence of 1/f noise. A common way to avoid such low frequency noise of system components, for example 1/f laser excess noise, is to shift the absorption signal to a higher frequency. In TDLAS technique, this can be achieved by a modulation of the diode laser operation current. Such modulation results in a modulation of the instantaneous laser frequency. Upon interaction with the non-linear reflected intensity profile of an absorption line, this will result in a periodic modulation of the detected intensity. This allows detection of absorption signal at the fundamental modulation frequency or its overtones.

For example a sinusoidal modulation of the diode laser operation current results in a sinusoidal wavelength (and amplitude) modulation of the laser output. Interaction with a wavelength-dependent and non-linear reflection signal (e.g. absorption line-shape) results in a periodic, but non-sinusoidal, reflection signal that consists of the modulation frequency itself as well as its harmonic overtones. This can be used in an embodiment to shift the detection frequency to the high frequency region less affected by low frequency noise (e.g. 1/f noise), and thus improving the sensitivity. This is typically achieved by letting a lock-in amplifier measure the amplitude of the harmonic components (most commonly, the second) as the laser is tuned over an absorption line of interest.

Also temperature of the detector detecting the reflected beams is advantageously decreased in order to minimize the noise. Additionally the light source, advantageously a laser, is kept in a constant temperature ensuring that the emitted wavelength is not changed arbitrarily.

Additionally, according to an embodiment, the gas concentration can also be measured additionally to the previous embodiments by:
  creating rapidly alternating high voltage,
  locally applying the rapidly alternating high voltage to the spacing of the glass unit to achieve local emission,
  collecting and transporting emitted light,
  determining the intensities of at least two different spectral intervals, at least one of which corresponds to the gas component of interest,
  calculating the ratio between the intensities of two spectral intervals, one of which corresponds to the gas component of interest, and
  determining the concentration of the gas component from said ratio.

According to an embodiment the measuring result may be written into a memory means coupled with the measured object, such as a glass unit. The memory means may be e.g. an RFID tag, or advantageously a NFC tag connected to the glass unit, wherein the stored measuring result may indicate e.g. one of the following property:

interface type of the object,
  coating material between two interfaces,
  refractive index of the constituent material,
  thickness of a layer between two interfaces,
  change of the thickness of a layer between two interfaces,
  distance between the first and second panes, such as outermost and innermost panes,
  possible toughening or tempering of any surface,
  existence and location of coated and/or non-coated surface of the object,
  concentration of at least one gas component in a gas mixture contained inside the glass unit, and/or
  identification information (such as location) of said spacing comprising the gas component.

According to an embodiment a narrow-bandwidth laser is scanned across an absorption line of the gas, and a detector is used to record the intensity profile of the reflected or transmitted beams. In order to increase sensitivity, modulation techniques, such as WMS or FWM, are employed. The strength of the gas absorption will depend, as given by the Beer-Lambert law, both on the gas concentration and the path-length that the light has travelled through the gas, so according to an embodiment also the pathlength is determined e.g. from the positions where the reflected beams hits the detector (this is possible, when the angle of the emitted beam is known or the measuring device is calibrated by these information). Another way is to use the unit with emitting means and detector and change the distance of said unit from the surface(s) of the glass unit or the mutual angle of the light emitting means and the detector of said unit. After this the concentration of the gas component can be determined.

According to an additional embodiment the gas component concentration can also be determined by:

determining the location and the intensity of the first reflected light beam (reflected from the first surfaces/interfaces of the glass sheets faced towards said spacing, whereupon the beam is not interacted with the gas component) on the detector,
  determining the location and the intensity of the second reflected light beam (reflected from the second or further surface/interface of the glass sheets faced towards said spacing or from the reflector) on the detector,
  determining the distance the beam has traversed within the spacing based on the locations of said first and second (or further) determined reflected beams on the detector, and
  determining the concentration of the gas component in said spacing based on the intensity difference of the first and second determined reflected beams and the traversed distance.

It is to be noted that the locations of the surfaces (and thereby the distances of them) can also be determined by changing the distance of the unit with the light emitting means and detector from the surfaces (or their mutual angle) and determining intensity maxims corresponding reflections from said surfaces when changing said distance of the unit (or the angle), as is illustrated e.g. in FIGS. 2C and 2D.

The first reflection can be used for compensating the effect of the first sheet and possibly any absorption occurring between the laser source and a surface or between the surface and the detector. It is to be noted that the embodiment above can be utilised in other embodiments of the invention disclosed in this document.

In addition, as discussed above the incident light beam emitted by the light source may be reflected from the several surfaces of the object, whereupon number of beams (corresponding to the number of the surfaces) are received and detected. The same principle can be implied as earlier for each surfaces of the object for determining whether any of these surfaces is the low emissivity surface and in which spacing the gas component causes said determined intensity variation (if any).

According to an embodiment thickness of the transparent object as well also thickness of constituent materials of the surface of the transparent object, as well as also thickness of other layers, can be detected based on the positions of the reflected light beams from the different layers of said object on the light sensitive electronic device (detector), when the distance between the separate reflected rays on the detector, the angle the incident beam hits the object and the refractive index of the material are known. Also the unit with fixed light emitting means and the detector may be used, when their distance (or angle) for the surfaces is varied and the intensity maxims is determined, as is illustrated in connection with e.g. FIGS. 2C, 2D.

Furthermore according to an embodiment an interface type of the glass unit, such as air-glass, glass-plastic, glass-Low-E coating or glass-glass type, can be detected. The interface type determination is advantageously based on the reflections from each interface layer, because each interface layer causes a reflection so that the position the reflected light beam from each interface layer hitting the detector depends on the type of interface in question. It should also be noted that also the intensity of the reflected beams depends on the interface type from which the beam is reflected.

According to an advantageous embodiment of the invention even information about the thickness of the layer of the object is not needed because the interface type (e.g. air-glass) can be determined purely from the intensity of the reflected beam. Since it is known beforehand that the incident beams will reflect first from the air-glass interface the next interface types can be determined from the intensities of the next reflections (reflections from the next surfaces), because the characteristic intensities for commonly used interface types are known beforehand. For example intensity of the beam reflected from the glass-air interface is clearly distinguishable from the intensity of the beam reflected from the glass-plastic or Low-E coating interface. Thus also the media of the object (or constituent material, such as glass or plastic, between the two interfaces) can be determined based on the intensities of the reflections. Again when the constituent material is known also the refractive index of each layer can be detected, and by using the determined refractive index for example the thickness of each layer can be calculated when the distance between the reflected beams on the detector is determined.

According to an embodiment the refractive indexes of typical media, such as glass, air, plastic and laminate coatings are advantageously stored into the memory means of the measuring device, which can be used in determination of the interface types. According to an embodiment the refractive index for each media layer of the object may be determined based on the intensities of the reflections only (since the first media, namely air, is always known) and then to use the accurate reflective index of typical media stored into the media means which seems to best correlate with the calculated reflective index. This is a convenient way to manage the determination since the fully accurate measurement for reflective index based only on the reflection intensities is not always possible due to the absorption of the media for example.

In addition the average reflection intensity can be used for determining the interface type by comparing the average reflection intensities to the known reflection intensities caused by known interface types when moving the apparatus in relation to the object. The reflection intensities depends of course for example about the used light source and angle the incident light hits the object, but these can be detected beforehand and taken into account in determination of the interface type in question.

The invention offers many advantageous features over the known prior art methods. Using multiple reflections (reflections from plurality of surfaces or interfaces) the quantity of information of the measured structure and the gas concentration increases and equally the accuracy of the results increases. In addition the measurements can be done for numbers of transparent spaces even though there exists or does not exist different kinds of coatings in the glass unit to be measured. Moreover the method of the invention can be used either to determine the gas concentration (especially $O_2$) in the spaces of the glass unit, but at the same time alto to determine the structure of the glass unit.

BRIEF DESCRIPTION OF THE DRAWINGS

Next the invention will be described in greater detail with reference to exemplary embodiments in accordance with the accompanying drawings, in which.

DETAILED DESCRIPTION

Figure 1A:
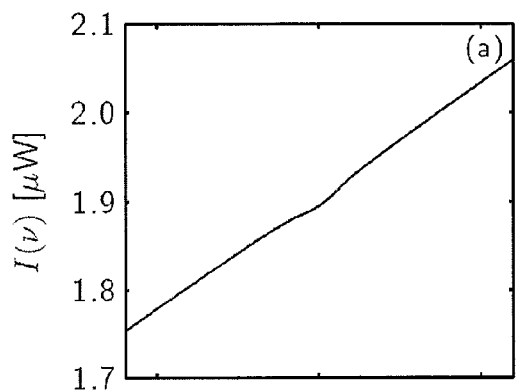
FIG. 1(a) shows detected intensity I(ν) of the reflected beam, where the weak absorption is barely seen.
Figure 1B:
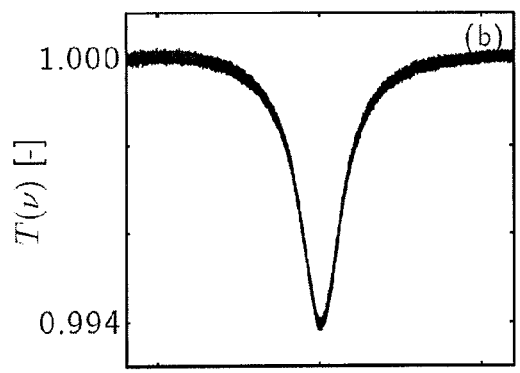
FIG. 1(b) shows the intensity of said reflected beam calculated using a second-order baseline estimation of $I_0(\nu)$ (i.e. a $2^{nd}$ order polynomial fitted to the edges of the detected signal)

FIGS. 1(a) and 1(b) relates to measurements and phenomena known from prior art, and are discussed earlier in this document.

FIGS. 2a-2e illustrates principles of exemplary measuring constructions 200 for determining a gas component concentration inside a transparent structure according to an advantageous embodiment of the invention.

According to an embodiment of the invention an apparatus comprises a light source 201 for emitting at least one light beam to the surface of the object, such as a glass unit 202. The light source is advantageously a narrow-band light source, which could be e.g. Vertical Cavity Surface Emitting Laser (VCSEL). The wavelength of emitted laser may be controlled e.g. by current by an adjustable current source 203. According to an embodiment the laser beam emitted 204 is modulated by introducing a modulation waveform to the current controller of the laser source (e.g. by WMS technique). For example an arbitrary waveform generator 205 can be used.

WMS is a high-resolution laser absorption technique, in which the absorption signal is moved to higher detection frequencies in order to avoid low-frequency noise of system components. In TDLAS this is realized by scanning a sinusoidally frequency-modulated diode laser over some narrow (e.g. gas-phase) absorption feature. This feature acts as a non-linear transfer function, producing a periodic but not perfectly sinusoidal variation in transmission (i.e. harmonic generation takes place overtones are generated). A WMS signal measures the temporal evolution in the amplitude of the harmonic frequencies and has traditionally been acquired using lock-in amplification. The usefulness comes with the fact that the WMS signal is proportional to the absorption (and thus gas concentration, in the case of weak absorption).

The light beams 207 reflected from different surfaces of each sheets 206a, 206b, 206c or other interfaces is then collected by a detector 208, such as e.g. by a CCD- or CMOS-sensor or by a photodiode(s). The resulting voltage signal is typically sampled coherently using an A/D board. Sensitivity is advantageously increased by using a second channel to record a high-pass (HP) filtered and amplified (A) signal version. A lock-in amplifier (or other suitable measuring means) 209 is used for measuring the amplitude of the harmonic components (most commonly, the second) as the laser is tuned over an absorption line of interest.

Figure 2A:
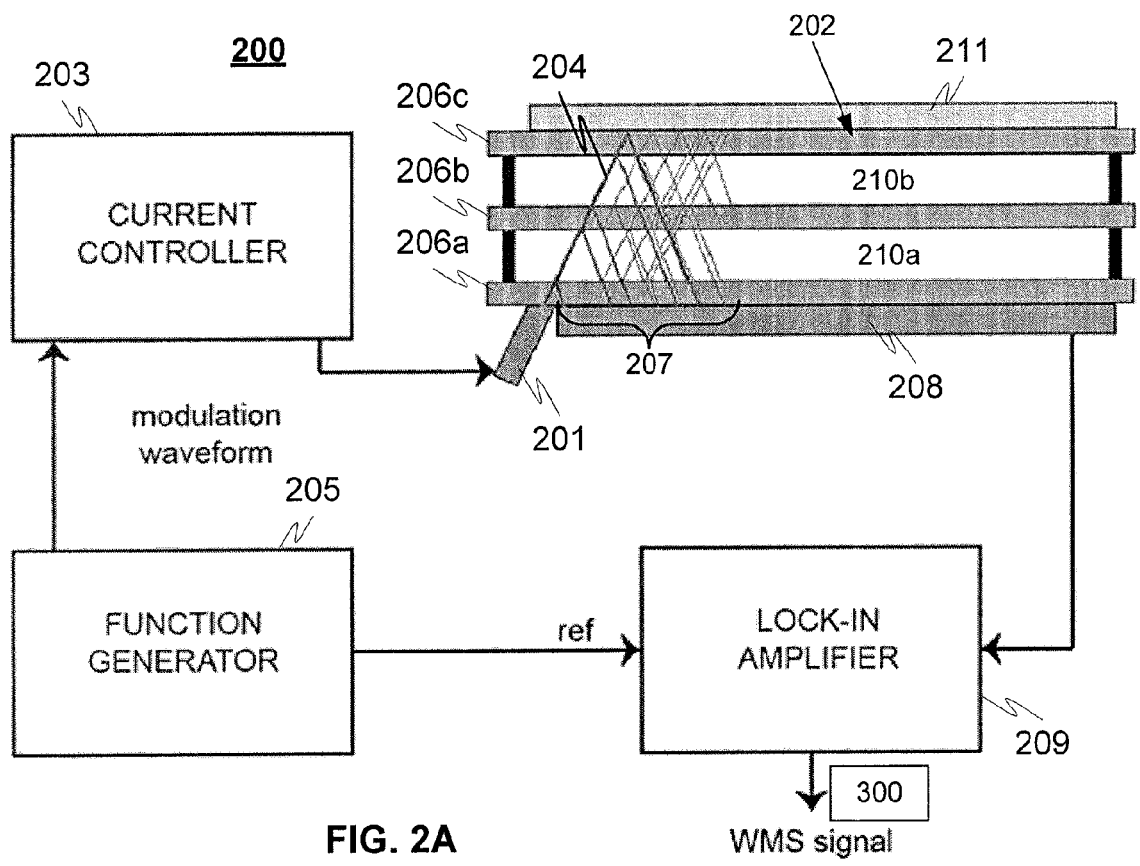
FIGS. 2a-e illustrates principles of exemplary measuring constructions for determining a gas component concentration inside a transparent structure according to an advantageous embodiment of the invention.
Figure 2B:
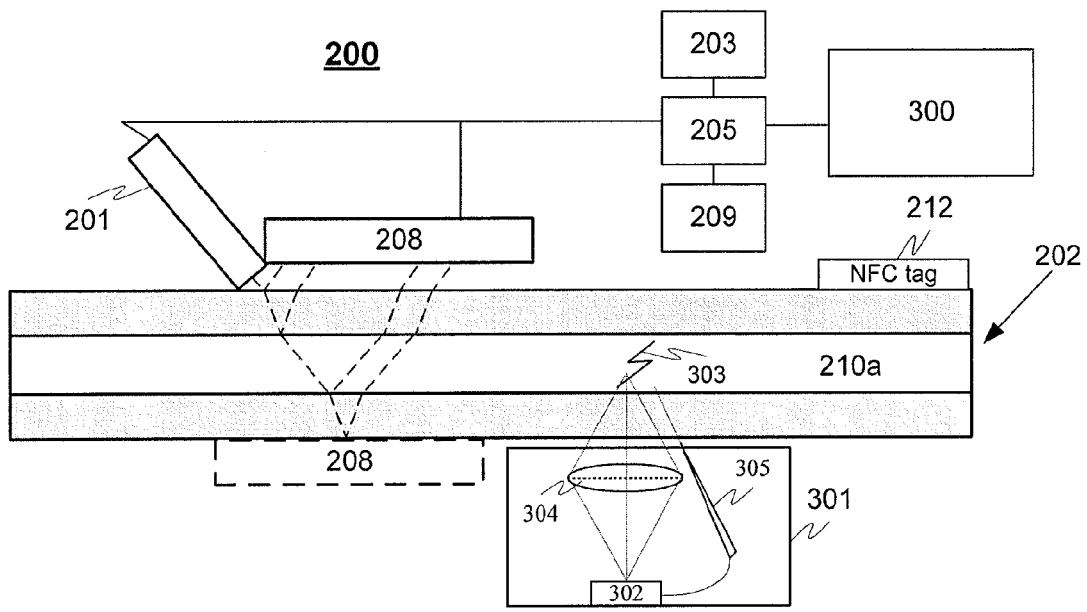

It is to be noted that according to the embodiments illustrated in FIGS. 2A-2B the number of reflections 207 from different surfaces can be received by the detector 208. However, the surface from which each of the reflection originates can be determined by the position of the received signal on the detector, namely the first reflection hit the detector is from the back side of the first sheet (not interacted with the gas in the spacings 210a or 210b), the second reflection hit the detector is from the first surface of the second sheet faced towards the first spacing 210a possibly containing the gas component to be measured, etc. Thus the second reflection is already interacted with the gas contained in the first spacing, etc., and thereby the gas concentration in each spacings 210a, 210b can be determined by determining a certain reflections interacted with said spacing in question.

When the incident angle of the emitted laser beam is known, the location of each surfaces caused the corresponding reflection can be determined and thereby also the distance the reflected light has travelled.

Also a reflector 211 can be utilised, as discussed elsewhere in this document.

FIG. 2B illustrates another construction, where the measuring arrangement comprise a data processing means 300, such as a microprocessor, for determining the measured intensities as well as also the positions of the reflected beams on the detector, and for calculating or determining the properties of the object and different parameters, such as interface types, constituent materials, refractive indexes and especially the concentrations of the gas components in different spaces of the glass unit, as discussed elsewhere in this document. In addition the arrangement may comprise another additional control means for controlling the light source and/or the detector, as well as memory means for storing for example intensities of reflections caused by different gas concentrations, interface types, constituent materials as well as also refractive indexes of these materials among the others. The arrangement 300 may also comprise means for reading and/or writing e.g. measuring information into a memory means of the measured object, such as a NFC tag 212 coupled with the glass unit.

The measuring arrangement 200 may also comprise an additional means 301 for detecting the concentration of at least one gas component in one spacing of the glass unit. The additional gas detecting means 301 advantageously comprises means 302 for creating rapidly alternating high voltage, which is advantageously locally applied to the spacing 210a of the glass unit to achieve local emission 303 by ionizing the atoms of the filling gas. In addition the detecting means comprises means 304 for collecting and transporting emitted light for determination and analysing the intensities advantageously of at least two different spectral intervals, at least one of which corresponds to the gas component of interest. In the ionizing method the arrangement (such as means 300 or 301) is advantageously adapted to calculate the ratio between the intensities of two spectral intervals, one of which corresponds to the gas component of interest, and thereby determine the concentration of the gas component from said ratio.

Rapidly alternating electrical field can be applied e.g. to the glass unit by using a needle-like electrode 305, for example. As the other electrode, for example a conducting layer of the object can be used. The rapidly alternating electrical field produces a discharged channel 303 in the spacing 201a, and the discharge starts in the close vicinity to the end of the electrode 305. Emitted light is collected advantageously by a lens 304.

In the embodiments illustrated in FIGS. 2A, 2B the distances from the reflecting surfaces (and thereby the thickness of the surfaces or interfaces or the spacings) are determined by the angle the light beam is emitted towards said surface and by the locations of the reflected beam on the detector 208.

Figure 2C:
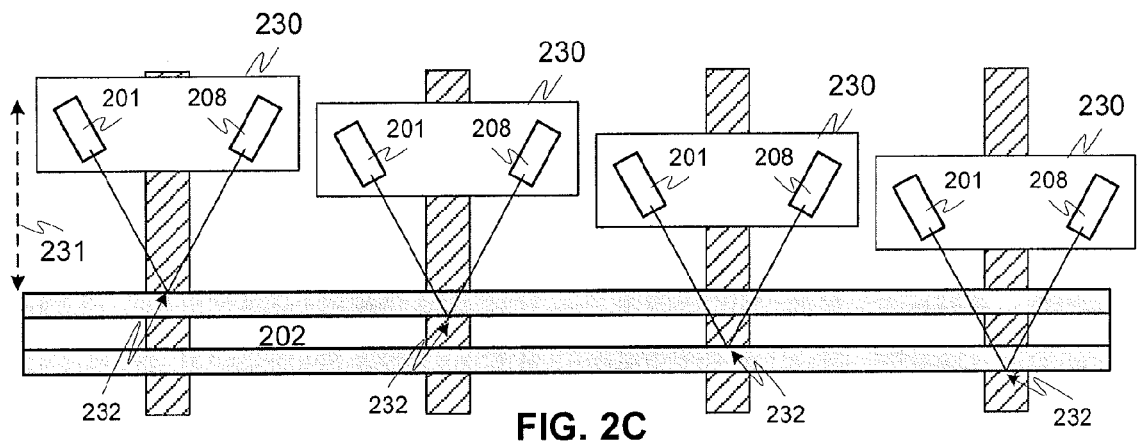
Figure 2D:
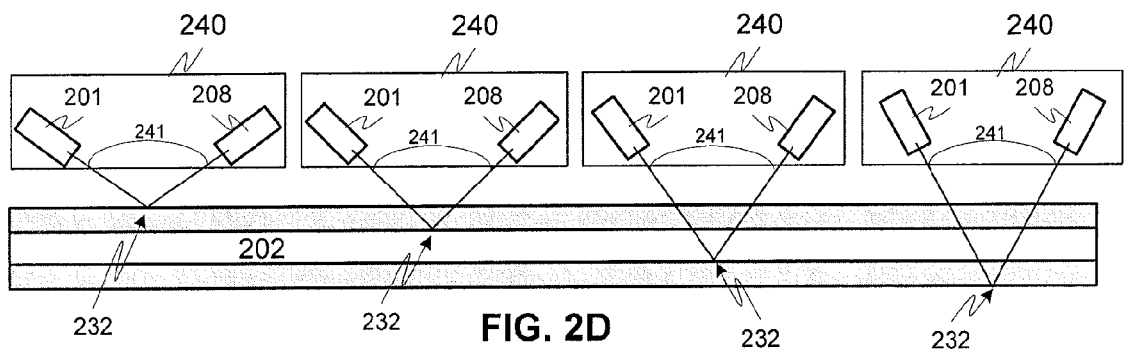

FIGS. 2C and 2D, however, illustrates another embodiment for the measuring the distances of the surfaces (and thereby thicknesses as well as other parameters). According to first aspect (FIG. 2C) the device 200 comprises a unit 230, which comprises both the light emitting means 201 as well as also the detector 208, which are advantageously fixedly mounted to the unit 230. The distance 231 of the unit 230 is configured to be varied in relation to the glass unit 202 or its surfaces, as is demonstrated in FIG. 2C. When the distance 231 is changed, also the focus spot 232 of said emitted light beam is changed. When the focus spot is shifted to hit to any of the surfaces of said glass unit, it is determined as intensity maximum and the distance (or location) of said surface can be determined by the distance change 231 of said unit.

According to second aspect (FIG. 2D) the device 200 comprises a unit 240, which comprises both the light emitting means 201 as well as also the detector 208, which are advantageously mounted to the unit 240 so that the angle 241 of emitted light beam (or the relative angle of the light emitting means and the detector) can be changed. The angle 241 is configured to be varied in relation to the glass unit 202 or its surfaces, as is demonstrated in FIG. 2D. When the angle 241 is changed, also the focus spot 232 of said emitted light beam is changed. When the focus spot is shifted to hit to any of the surfaces of said glass unit, it is determined as intensity maximum and the distance (or location) of said surface can be determined by the angle change 241. Thus also with the embodiments illustrated in FIGS. 2C and 2D the orders of the intensity maxims correlates with the (order of the) interfaces reflecting said beams.

Figure 2E:
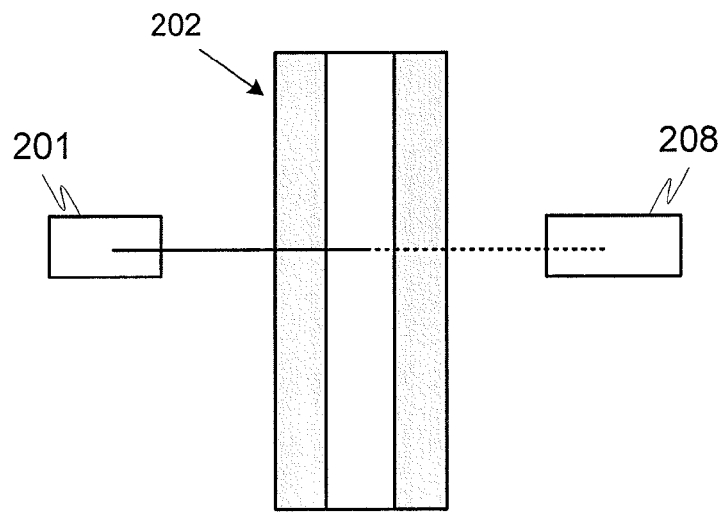

In addition it is to be noted that according to an embodiment also transmission measurement is possible, as is illustrated in FIG. 2E, where the light emitting means 201 locates at the different side of the glass unit 202 to be measured than the detector 208. This enables a very simple structure of the device 200, since there is no need for moving and light emitting means 201 and the detector 208 in relation to each other and also the focusing is very straightforward. Also the detected signal is typically much more powerful. However, only the total absorption can be determined.

Figure 3:
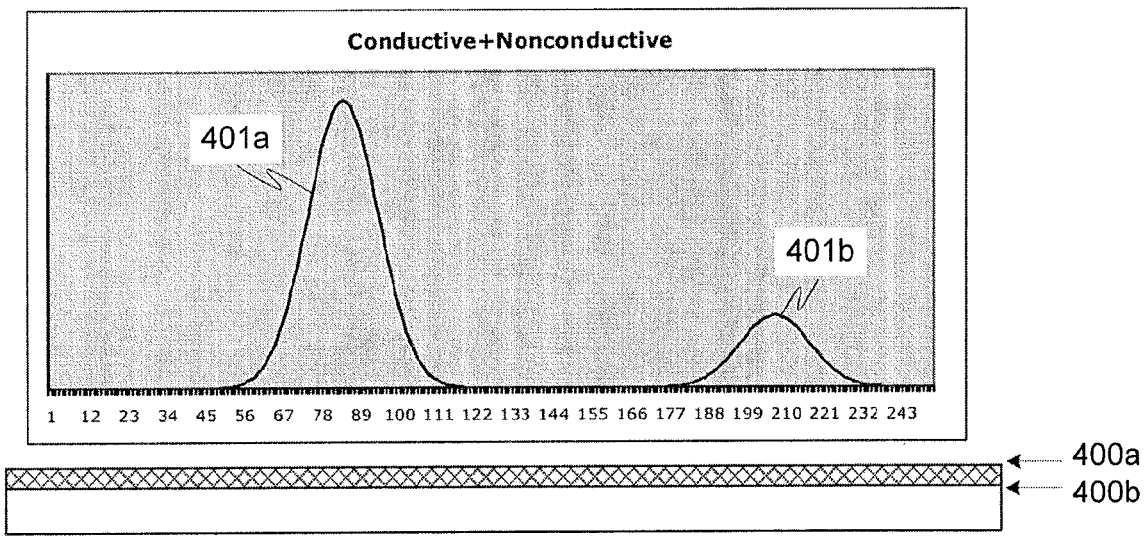
FIG. 3 illustrates exemplary intensities for a conductive and non-conductive surfaces measured according to an advantageous embodiment of the invention.

FIG. 3 illustrates exemplary intensities 401a, 401b for a conductive 400a and non-conductive 400b surfaces measured according to an advantageous embodiment of the invention, where the conductive surface 400a reflects the beam of high intensity 401a compared to the non-conductive surface 400b reflecting the beam of low intensity 401b.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. Even though only a glass unit is described above, it is to be noted that different kinds of reflective transparent objects can be determined, such as for example a glass or plastic, such as float glass, laminated glass, toughened or tempered glass, especially an insulating glass or glass coated with a coating, for instance an electrically conductive coating.

In addition it is to be noted that the wavelength of the emitted light beam can be varied also around or over a secondary absorption line of the interest gas component, namely operating e.g. the TDL (Tunable Diode Laser) transmitter at a secondary absorption line (e.g. of lower strength) effectively simulates measurement of a lower concentration of oxygen. For example wavelength of the light of the light source may further be varied such that the wavelength is adapted to coincide with at least one other absorption maximum (peak) with different absorption properties of the gas, e.g. oxygen, to be measured, and correspondingly the attenuation of the other absorption maximum or maxima is measured as a function of the wavelength of the light. The device or arrangement may also comprise a computer program product adapted to perform method step for determining a concentration of a gas component, when said program is run on the devise or arrangement.

Furthermore it is to be noted that different kinds of lenses can be used in connection with the light emitting means in order to focus the emitted beams onto the surfaces, as well as also in connection with the detector to focus the collected light beams onto the surface of the detector. This enables more powerful signal gathered and thereby e.g. concentration measurement of $O_2$ is more reliable.

The invention claimed is:

1. A non-invasive method for determining a concentration of a gas component in a gas mixture contained in a spacing of a glass unit having at least two glass sheets spaced apart from each other and forming said spacing, the method comprising:
   applying one or more light beams at an angle to the surface of said glass unit, wherein the wavelength of the emitted light beam is varied around or over the at least one absorption line of the interest gas component,
   collecting by a detector the light beams transmitted through or reflected from at least one surface or interface locating at the opposite side of the spacing,
   determining non-linear variations in the intensity of the transmitted or reflected light beams over an absorption line of the interest gas component to be determined, and
   determining the concentration of the gas component based on said non-linear variations in the intensity.

2. The method of claim 1, wherein the concentration determination is implemented by comparing the quantity of the non-linear intensity variations to reference intensity variations, such as the intensity variations of different concentrations of said gas known beforehand.

3. The method of claim 1, wherein the surface or interface reflecting the beam is a reflector used at the opposite side of the glass unit for reflecting the emitted light beam through the glass unit on the detector, whereupon the measured gas concentration inside the glass unit is detected from the intensity variation at the absorption line(s) when varying the wavelength of the emitted light beam over the absorption line(s).

4. The method of claim 1, wherein the surface or interface reflecting the beam is a surface or interface of the glass sheet faced towards said spacing comprising the gas component.

5. The method of claim 1, wherein the spacing comprising the gas component concentration and thereby causing said non-linear intensity variation is determined by orders or positions of the beams on the detector reflected from the surfaces or interfaces of the glass sheets of the glass unit.

6. The method of claim 1, wherein the method further comprises determining interface type and/or possible coatings of the glass sheet in question by measuring the intensity of the beam reflected from said interface, comparing the measured intensity to the known intensities of known interface type and/or coating types and selecting the interface type and/or coating type the known intensity of which best matches with the measured intensity.

7. The method of claim 1, wherein the method further comprises:
   detecting the thickness of a layer between two interfaces of the glass unit based on the locations of the light beams reflected from the first and second interfaces on the detector,
   detecting the distance between two sheets, such as outermost and innermost sheets, based on the locations of the light beams reflected from the corresponding sheets on the detector and the refractive index of said material of the sheets.

8. The method of claim 1, wherein the locations and thereby distances of surfaces or interfaces of said glass unit is measured by a measuring unit comprising the light emitting means and the detector, which distances from the surfaces or interfaces are varied or angles of which are changed in relation the surfaces or interfaces, and wherein the intensity variations are determined in order to determine said locations and thereby distances of said surfaces or interfaces based on said intensity maxims.

9. The method of claim 1, wherein the light beams are laser light beams provided by a tunable-diode-laser-absorption-spectroscopy (TDLAS) technique by tuning the used laser frequency over an absorption line of interest gas component.

10. The method of claim 9, wherein the absorption signal to be detected is manipulated by WMS or FMS technique, such as by scanning a sinusoidally frequency-modulated diode laser over the absorption feature of the gas component to be determined in order to strengthen the second order polynomial fitted to the nonlinear curve representing the variation in the intensity of the detected beams and concentration of the gas component to be detected and/or to minimize the low-frequency noise induced.

11. The method of claim 1, wherein the method further comprises:
   creating rapidly alternating high voltage,
   locally applying the rapidly alternating high voltage to the spacing of the glass unit to achieve local emission,
   collecting and transporting emitted light,
   determining the intensities of at least two different spectral intervals, at least one of which corresponds to the gas component of interest,
   calculating the ratio between the intensities of two spectral intervals, one of which corresponds to the gas component of interest, and
   determining the concentration of the gas component from said ratio.

12. The method of claim 1, wherein said gas component to be measured is at least one of the following: Oxygen, Argon, Xenon, Krypton and/or Nitrogen.

13. The method of claim 1, wherein the measuring result is written into an NFC tag connected to said glass unit, the measuring result indicating at least one of the following property:
   interface type of the object,
   coating material between two interfaces,
   refractive index of the constituent material,
   thickness of a layer between two interfaces,
   change of the thickness of a layer between two interfaces,
   distance between the first and second panes, such as outermost and innermost panes,
   possible toughening or tempering of any surface,
   existence and location of coated and/or non-coated surface of the object,
   concentration of at least one gas component in a gas mixture contained inside the glass unit, and/or
   identification information of said spacing comprising the gas component.

14. An arrangement for non-invasively determining a concentration of a gas component in a gas mixture contained in a spacing of a glass unit having at least two glass sheets spaced apart from each other and forming said spacing, the arrangement being adapted to:
   apply one or more light beams at an angle to the surface of said glass unit, and varying the wavelength of the emitted light beam around or over the at least one absorption line of the interest gas component,
   collect by a detector the light beams transmitted through or reflected from at least one surface or interface locating at the opposite side of the spacing,
   determine non-linear variations in the intensity of the transmitted or reflected light beams over an absorption line of the interest gas, and
   determine the concentration of the gas component based on said non-linear variations in the intensity.

15. The arrangement of claim 14, wherein the arrangement is adapted to determine the concentration by comparing the quantity of the non-linear intensity variations to reference intensity variations, such as the intensity variations of different concentrations of said gas known beforehand.

16. The arrangement of claim 14, wherein the arrangement is adapted to determine the spacing comprising the gas component concentration and thereby causing said non-linear intensity variation by orders or positions of the beams on the detector reflected from the surfaces or interfaces of the glass sheets of the glass unit.

17. The arrangement of claim 14, wherein the arrangement comprises a measuring unit comprising the light emitting means and the detector, which distances from the surfaces or interfaces are configure to be varied or angles of which are configured to be changed in relation the surfaces or interfaces, and wherein the arrangement is configured to determine intensity variations in order to determine locations and thereby distances of the surfaces or interfaces of the glass unit to be measured based on the intensity maxims.

18. The arrangement of claim 14, wherein the arrangement is adapted to determine interface type and/or possible coatings of the glass sheet in question by measuring the intensity of the beam reflected from said interface, comparing the measured intensity to the known intensities of known interface type and/or coating types and selecting the interface type and/or coating type the known intensity of which best matches with the measured intensity.

19. The arrangement of claim 14, wherein the arrangement comprises a tunable-diode-laser (TDLAS) and is adapted to tune the used laser frequency over an absorption line of interest gas component.

20. The arrangement of claim 14, wherein the arrangement is adapted to manipulate the absorption signal to be detected by WMS or FMS technique, such as by scanning a sinusoidally frequency-modulated diode laser over the absorption feature of the gas component to be determined in order to strengthen the second order polynomial fitted to the non-linear curve representing the variation in the intensity of the detected beams and concentration of the gas component to be detected and/or to minimize the low-frequency noise induced.

21. The arrangement of claim 14, wherein the arrangement further comprises means for:
   creating rapidly alternating high voltage,
   locally applying the rapidly alternating high voltage to the spacing of the glass unit to achieve local emission,
   collecting and transporting emitted light,
   determining the intensities of at least two different spectral intervals, at least one of which corresponds to the gas component of interest,
   calculating the ratio between the intensities of two spectral intervals, one of which corresponds to the gas component of interest, and
   determining the concentration of the gas component from said ratio.

* * * * *